United States Patent [19]
Tusini et al.

[11] Patent Number: 5,431,811
[45] Date of Patent: Jul. 11, 1995

[54] ARTIFICIAL KIDNEY WITH DEVICE FOR FILTERING DIALYSIS LIQUID

[75] Inventors: Andrea Tusini, Modena; Luca Vinci, Poggio Rusco, both of Italy

[73] Assignee: Hospal AG, Switzerland

[21] Appl. No.: 62,766

[22] Filed: May 18, 1993

[30] Foreign Application Priority Data

May 19, 1992 [FR] France ................... 92 06329

[51] Int. Cl.⁶ ............ B01D 61/28; B01D 61/32; B01D 65/10
[52] U.S. Cl. ........................... 210/90; 210/97; 210/117; 210/130; 210/134; 210/143; 210/195.2; 210/254; 210/321.69; 210/420; 210/424; 210/433.1; 210/435; 210/929; 364/413.01; 364/413.02; 604/4
[58] Field of Search ............ 210/90, 97, 111, 117, 210/130, 134, 143, 195.2, 196, 254, 257.2, 258, 259, 321.69, 321.71, 321.72, 321.75, 321.84, 409, 416.1, 420, 424, 433.1, 435, 929; 364/413.01, 413.02; 604/4; 137/119

[56] References Cited
U.S. PATENT DOCUMENTS

| | | |
|---|---|---|
| 3,506,126 | 4/1970 | Serfass et al. ............ 210/254 |
| 4,113,614 | 9/1978 | Rollo et al. ............ 210/90 |
| 4,202,764 | 5/1980 | Afflerbaugh et al. ............ 210/929 |
| 4,252,651 | 2/1981 | Soderstrom ............ 210/97 |
| 4,298,938 | 11/1981 | Wang et al. ............ 210/90 |
| 4,606,826 | 8/1986 | Sano et al. ............ 210/929 |
| 4,735,727 | 4/1988 | Heitmeier et al. ............ 210/321.71 |
| 4,753,733 | 6/1988 | Ramstack ............ 210/637 |
| 4,834,888 | 5/1989 | Polaschegg ............ 210/646 |
| 4,936,980 | 6/1990 | Harada: Yoshimichi et al. ... 210/90 |
| 5,147,552 | 9/1992 | Hlavacek et al. ............ 210/111 |

*Primary Examiner*—John Kim
*Attorney, Agent, or Firm*—Finnegan, Henderson, Farabow, Garrett & Dunner

[57] ABSTRACT

A filtration device includes an ultrafilter having an inlet chamber, an outlet chamber, and an ultrafiltration membrane separating the inlet chamber from the outlet chamber. An inlet line flow connects the inlet chamber to a source of dialysis liquid. Pressure sensors determine pressure values on opposite sides of the membrane, and a controller calculates a transmembrane pressure therefrom and compares the calculated transmembrane pressure with a predetermined threshold value. If the threshold value is reached, the controller emits a threshold signal to either warn an operator or alternatively to automatically divert flow to bypass the ultrafilter.

20 Claims, 1 Drawing Sheet

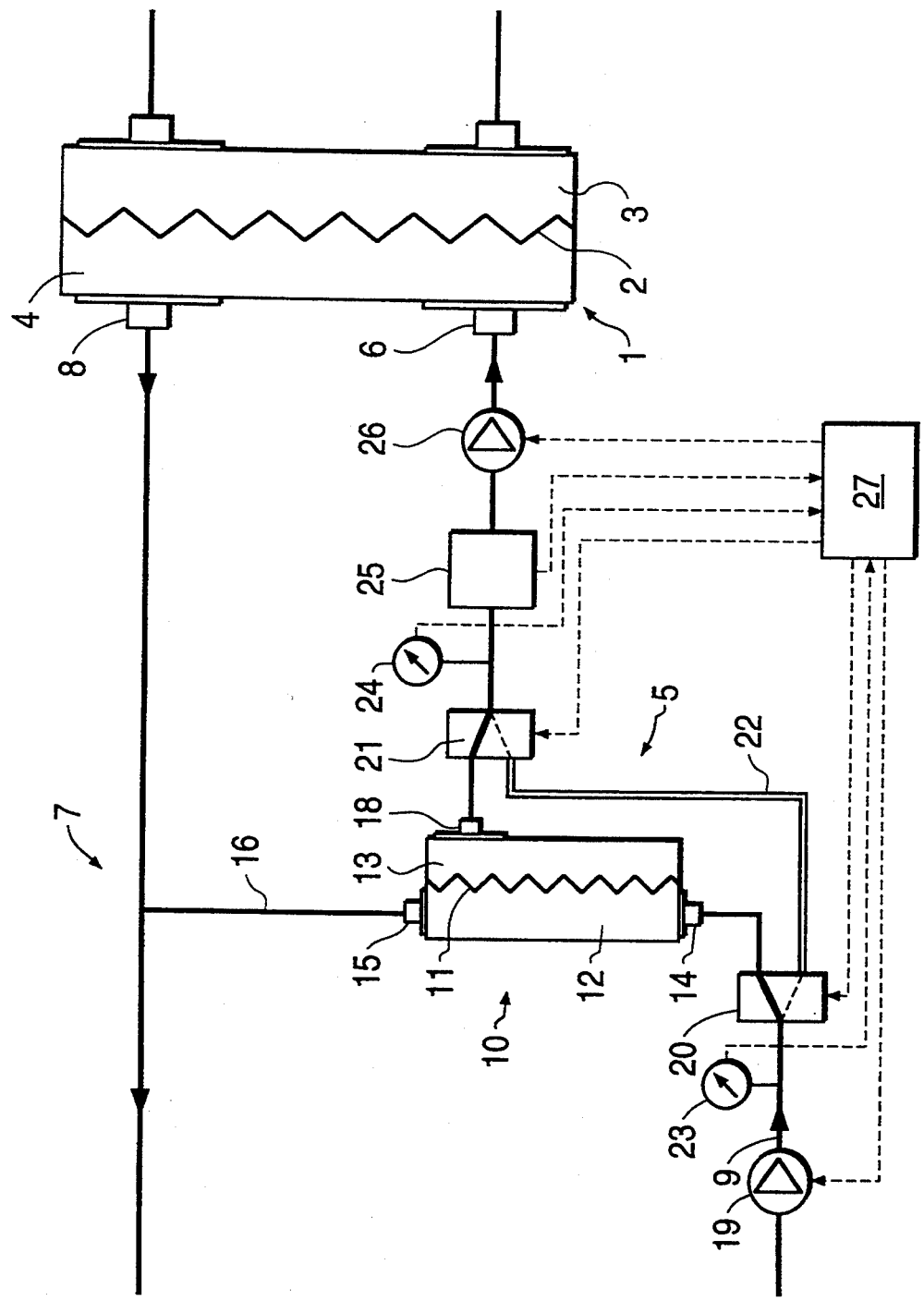

ARTIFICIAL KIDNEY WITH DEVICE FOR FILTERING DIALYSIS LIQUID

BACKGROUND OF THE INVENTION

1. Field of the Invention

The present invention relates to the field of extracorporeal treatment of blood by dialysis and/or by ultrafiltration. More particularly, the invention relates to a hydraulic circuit for an artificial kidney in which the dialysis-liquid circuit includes an ultrafilter intended to rid the dialysis liquid of microorganisms and possibly pyrogenic elements which it might contain.

2. Description of the Related Art

With the development of high-permeability haemodialyzers, there has been increased interest in the use of dialysis liquid having good biological properties to protect against blood contamination which may occur if portions of the dialysis liquid enter the blood stream. While exchanges in a haemodialyzer during blood purification are intended to only occur from the blood compartment toward the dialysis-liquid compartment, the possibility remains of having, on the contrary, a transfer from the dialysis liquid towards the blood. This may occur either by diffusion or by convection in situations where the pressure in the dialysis-liquid compartment becomes greater than the pressure in the blood compartment.

U.S. Pat. No. 4,834,888 discloses an artificial kidney comprising a filter for in-line sterilization of dialysis liquid before its entry into the haemodialyzer. According to this document, the filter used for sterilizing the dialysis liquid comprises two compartments separated by a membrane capable of retaining germs. The liquid coming from a dialysis-liquid source is completely filtered through this filter before entering the haemodialyzer. In order to avoid filter clogging, the compartment connected to the dialysis-liquid source is rinsed at the end of each haemodialysis session, and may also be rinsed during a session as well.

For this purpose, this compartment has an output connected to a line for draining the used dialysis liquid coming from the haemodialyzer. During the filter-rinsing phase, sterilizing the liquid by filtration is stopped, and the liquid entering the filter then sweeps along the surface of the membrane in order to detach the germs and pyrogenic elements which are deposited thereon. Thereafter, the liquid directly rejoins a line for draining the used dialysis liquid.

In order to check the integrity of the membrane of this sterilization filter, this document describes a specific test performed between two dialysis sessions. This test involves introducing air into at least one part of the dialysis-liquid circuit, and can therefore only be performed when the haemodialyzer is disconnected from the dialysis apparatus.

Thus, the device described in this document has the drawback of not allowing the integrity and efficiency of the membrane of the filter to be checked during use.

SUMMARY OF THE INVENTION

The subject of the present invention is a hydraulic circuit for an artificial kidney allowing continuous checking of the correct state of the ultrafilter without stopping its operation.

A subject of the present invention is also a hydraulic circuit for an artificial kidney allowing its user to be warned in case of clogging or breakage of the membrane filtering the dialysis liquid. For this purpose, the present invention provides a hydraulic circuit for an artificial kidney comprising at least one line connected to a dialysis-liquid source, and provided with at least one ultrafilter having two chambers separated by a membrane capable of retaining the microbial and pyrogenic elements. The first chamber is connected to a line which is connected to a dialysis-liquid source. The invention also includes means for determining the transmembrane pressure existing on either side of the membrane of the ultrafilter, means for fixing at least one threshold value for this transmembrane pressure, and means for comparing the transmembrane pressure value determined with the threshold value, in order to act on control means in the case where the transmembrane pressure value determined reaches the fixed threshold value.

Advantageously, the hydraulic circuit according to the present invention may further comprise means for sustaining a continuous tangential flow of liquid along the membrane of the ultrafilter. Thus, the deposition of microorganisms of pyrogenic elements and consequently the clogging of the membrane are reduced as much as possible thereby permitting the life of the ultrafilter to be increased while simultaneously decreasing the risk that undersirable elements will pass into the liquid entering the haemodialyzer or into the extracorporeal blood circuit, in situations where the membrane of the ultrafilter has been damaged.

According to a particular embodiment, the hydraulic circuit of the invention further comprises, downstream of the ultrafilter, means for precisely controlling the flow of liquid. Thus, whatever the pressure loss caused in the dialysis-liquid circuit by the presence of an ultrafilter, the flow rate of dialysis liquid entering the haemodialyzer or the extracorporeal blood circuit can be held constant.

According to another embodiment of the present invention, the hydraulic circuit further comprises a branch circuit allowing the dialysis liquid to short-circuit the ultrafilter. This is particularly advantageous when the liquid filtered is used as the dialysis liquid, because, when a defect in the integrity of the membrane is detected, it is not necessary to stop the treatment, but rather, it is possible to continue the session without exposing the patient to serious risks.

Other features and advantages will emerge in the description which follows, with reference to the drawing.

BRIEF DESCRIPTION OF THE FIGURE

FIG. 1 schematically illustrates an artificial kidney circuit in accordance with the present invention.

DESCRIPTION OF THE PREFERRED EMBODIMENT

In FIG. 1, a part of the artificial kidney is diagrammatically represented (only the elements relating to the invention have been represented), which comprises a conventional haemodialyzer 1 divided by membrane 2 into two compartments 3 and 4. Blood to be treated flows through compartment 3 and dialysis liquid for purifying the blood passes through compartment 4. The circuit for circulating dialysis liquid inside the artificial kidney comprises an upstream portion 5 for conveying fresh dialysis liquid entering haemodialyzer 1 through an inlet 6, as well as a downstream portion 7 for conveying used dialysis liquid leaving haemodialyzer 1 through an outlet 8. The upstream portion 5 of the dialysis-liquid circuit consists of a mainline 9 capable of conveying fresh dialysis liquid from a source (not shown) towards the haemodialyzer. Line 9 comprises an ultrafilter 10 having an ultrafiltration membrane 11 capable of retaining microorganisms and pyrogenic elements of the dialysis liquid.

Membrane 11 therefore separates the ultrafilter 10 into two compartments; a compartment 12 for receiving fresh dialysis liquid which may be contaminated, and a compartment 13 for collecting the ultrafiltered dialysis liquid.

Compartment 12 includes an inlet opening 14 for the dialysis liquid to be filtered, connected to line 9, as well as an outlet opening 15 for the unfiltered dialysis liquid, connected to line 16, itself connected to the downstream portion 7 of the dialysis-liquid circuit. Compartment 13 of ultrafilter 10 is provided with an outlet opening 18 for the filtered liquid.

Line 9 also comprises, upstream of the ultrafilter 10, a pump 19 for circulating the dialysis liquid. According to the invention, a pressure sensor 23 is arranged in line 9, upstream of the ultrafilter and downstream of the pump 19, which pressure sensor makes it possible to continuously measure the pressure of the dialysis liquid upstream of the ultrafilter.

Similarly, a pressure sensor 24 situated between the ultrafilter 10 and the haemodialyzer 1 makes it possible to continuously measure the pressure of the filtered dialysis liquid at the output of the ultrafilter.

Advantageously, a three-way valve is arranged on either side of the ultrafilter 10. Specifically, valve 20 is situated upstream of the ultrafilter 10 but downstream of the pressure sensor 23, whereas a valve 21 is situated downstream of the ultrafilter but upstream of the pressure sensor 24. These valves 20 and 21 are directly connected to each other by a branch line 22.

A flow meter 25 as well as a circulating pump 26 are arranged downstream of the pressure sensor 24. A control unit 27 receives the information coming from the pressure sensors 23 and 24 as well as from the flow meter 25, and controls the operation of the valves 20, 21, and of the pumps 19 and 26.

The artificial kidney, as described above, operates as follows. Dialysis liquid is circulated by the action of the pump 19 whose delivery is fixed for example at 0.54 l/min, with the valves 20 and 21 being positioned such that liquid circulates through the ultrafilter 10 and not through branch line 22. More specifically, the dialysis liquid flows through line 9, then enters the ultrafilter 10.

By virtue of the action of the pump 26 whose delivery is fixed for example at 0.5 l/min, a large fraction of the liquid entering ultrafilter 10 is filtered by passage through the membrane 11 and enters haemodialyzer 1 through inlet 6. The liquid then leaves haemodialyzer 1 through opening 8 and is conveyed, by virtue of the downstream portion of the dialysis-liquid circuit, towards drainage or regeneration means (not shown).

According to one characteristic of the invention, the pressure values measured by the sensors 23 and 24 and corresponding to the pressure values on the liquid on either side of the ultrafiltration membrane 11 are transmitted during a first mode of operation of the ultrafilter to the control unit 27 which thus determines the value of the transmembrane pressure. During the first mode of operation, dialysis liquid is prefiltered through ultrafilter 10 as discussed in greater detail above. This transmembrane pressure value (TMP) is compared with one or more threshold values previously recorded by the operator in the control unit as a function of the ultrafilter used. Thus, it is possible to fix an upper threshold value corresponding to clogging of the membrane 11, and a lower threshold value corresponding to damage of the membrane, such as breakage. If the TMP value calculated reaches one or the other of the threshold values, the control unit 27 emits a threshold signal intended to warn the operator, by triggering, for example, a visual and/or acoustic alarm, or by displaying a suitable message on a screen (not shown) acting as an interface between the operator and the machine. The operator may then act manually on the control means of valves 20 and 21 in order to operate them so that the dialysis liquid no longer flows through the ultrafilter 10 but follows the branch line 22 in accordance with a second mode of operation, whereby prefiltration by ultrafilter 10 is bypassed. Thus, the threshold values demarcate a desired switch-over-point from the first mode of operation to the second mode of operation, allowing the blood-treatment session to continue with unfiltered dialysis liquid until the operator has replaced the filter.

Alternatively, the control unit 27 may directly control the operation of the valves 20 and 21 when the transmembrane pressure calculated reaches one or other of the threshold values.

According to an advantageous characteristic of the invention, a fraction of the dialysis liquid entering the ultrafilter 10 does not pass through membrane 11, but emerges directly through opening 15 in ultrafilter 10 in order to rejoin, through line 16, the used dialysis liquid coming from haemodialyzer 1. This continuous tangential flow is obtained by virtue of the difference existing between the delivery provided by pump 19 and that of pump 26. Alternatively, it is possible to provide line 16 with a low-delivery pump (not shown) which allows the rate of the tangential flow to be controlled precisely. The continuous sweeping of the ultrafiltration membrane by a tangential flow of liquid has the advantage of carrying with it microorganisms, fewer of which are deposited on the membrane. This increases the life of the ultrafilter and reduces the risk that a large amount of microbial and/or pyrogenic elements will pass to the haemodialyzer in the event that the ultrafiltration membrane is damaged.

According to another characteristic of the invention, the flow of filtered dialysis liquid through membrane 11 is controlled very precisely, by virtue of, for example, pump 26 with very precise delivery, or by the addition of a flow meter 25 that transmits information to control unit 27 which consequently controls the operation of pump 26. This slaving of pump 26 to the flow rate measured by the flow meter 25 allows the flow of dialysis liquid entering haemodialyzer 1 to be held constant.

Numerous variant embodiments are within the capability of a person skilled in the art without departing from the scope of the present invention. For example, it is possible to provide for the transmembrane pressure several upper and lower threshold values corresponding to various degrees of clogging or damage of the ultrafiltration membrane, which require different actions on the part of the operator or the machine.

Similarly, it is possible to improve the precision of the flow rate of the liquid delivered by the circulation pump 19 by adding to line 9 a flow meter (not shown) to which the operation of the pump 19 would be slaved.

The present invention has been described in its particular application to the case where the filtered liquid is used as the dialysis liquid. It is also possible to apply the invention to situations where the filtered dialysis liquid is injected as a substitution liquid into the extracorporeal blood circuit. This may be the case during haemofiltration when blood purification is performed solely by ultrafiltration without circulation of dialysis liquid on a side of the membrane opposite to the circulating blood. Alternatively the invention can be used in connection with haemodiafiltration where blood is purified both by dialysis and by ultrafiltration with reinjection of a substitution liquid into the extracorporeal blood circuit.

What is claimed is:

1. An artificial kidney circuit responsive to a transmembrane pressure threshold value for switching between a first mode of operation wherein dialysis liquid is prefiltered before patient treatment and a second mode of operation wherein prefiltration is bypassed, the circuit comprising:
  an ultrafilter having an inlet chamber, an outlet chamber, and an ultrafiltration membrane separating the inlet chamber from the outlet chamber;
  a haemodialyzer having a dialysate compartment and a blood compartment separated from the dialysate compartment by a dialysis membrane;
  an inlet line for flow connecting the inlet chamber to a source of dialysis liquid;
  an outlet line for flow connecting the outlet chamber to the dialysate compartment of the haemodialyzer;
  a branch line for bypassing the ultrafilter, the branch line having a first end flow connected to the inlet line and second end flow connected to the outlet line;
  valve means for selectively diverting fluid flow from the inlet line into the branch line; and
  means for continuously checking the membrane of the ultrafilter while dialysis liquid flows from the source through the ultrafilter and the haemodialyzer to determine the existence of breaks and clogs, the checking means including means for determining pressure on opposite sides of the membrane, and for calculating a transmembrane pressure therefrom, means for storing the transmembrane pressure threshold value demarcating a desired switch-over-point from the first mode of operation to the second mode of operation, and control means for comparing the calculated transmembrane pressure with the stored threshold value and for generating a threshold signal when the calculated transmembrane pressure reaches the threshold value.

2. The circuit according to claim 1 wherein said control means includes means for emitting at least one warning signal.

3. The circuit according to claim 1 wherein the means for determining pressure includes a first pressure sensor upstream of the ultrafilter, a second pressure sensor downstream of the ultrafilter, a monitoring unit for receiving pressure signals from the first and second pressure sensors and for determining the transmembrane pressure therefrom.

4. The circuit according to claim 1 further comprising means for sustaining a continuous tangential flow of liquid along the membrane of the ultrafilter.

5. The circuit according to claim 1 further comprising downstream of the ultrafilter, means for precisely controlling liquid flow.

6. The circuit according to claim 5 wherein the means for precisely controlling the flow of liquid includes a circulation pump and a flow meter, the circulation pump being slaved to the flow meter.

7. The circuit according to claim 1 wherein the valve means includes a first valve located at the first end of the branch line and a second valve located at the second end of the branch line.

8. The circuit according to claim 7 wherein the control means includes means for controlling the first and second valves in order to selectively permit dialysis liquid to bypass the ultrafilter through the branch line.

9. The circuit according to claim 1 wherein the means for storing includes means for storing a high threshold value corresponding to a clogged membrane, and a low threshold value corresponding to a torn membrane, and wherein the control means generates a low threshold signal when the calculated transmembrane pressure reaches the low threshold value and a high threshold signal when the calculated transmembrane pressure reaches the high threshold value.

10. The circuit according to claim 8 wherein the control means further includes means for regulating the first and second valves to bypass the ultrafilter in response to the threshold signal.

11. The circuit according to claim 1, wherein the outlet chamber of the ultrafilter is flow connected to an extracorporeal blood circuit, the blood circuit being connected to a dual compartment exchanger.

12. An artificial kidney circuit comprising:
  an ultrafilter having an inlet chamber, an outlet chamber, and an ultrafiltration membrane separating the inlet chamber from the outlet chamber;
  an inlet line for flow connecting the inlet chamber to a source of dialysis liquid;
  an exchanger having a blood compartment, a purification liquid compartment and an exchanger membrane separating the blood compartment from the purification liquid compartment, the purification liquid compartment having an inlet opening and an outlet opening;
  a connecting line, flow communicating the outlet chamber of the ultrafilter with the inlet opening of the exchanger;
  an outlet line connected to the outlet opening of the exchanger;
  a branch line having a first end connected to the inlet line and a second end connected to the connecting line, thereby forming a direct path from the dialysis source to the exchanger, the path bypassing the ultrafilter;
  a first pressure sensor located in the inlet line for transmitting a first pressure signal;
  a second pressure sensor located in the connecting line for transmitting a second pressure signal; and
  a controller electrically connected to the first and second pressure sensors for receiving the first and second pressure signals and for calculating a transmembrane pressure of the ultrafiltration membrane, the controller also for storing a predetermined pressure threshold value, for comparing the calculated transmembrane pressure with the threshold value, and for generating a signal indicating that a threshold is attained when the calculated pressure reaches the threshold value.

13. An artificial kidney circuit according to claim 12 further including valve means flow connected to the branch line for diverting flow from the inlet line through the branch line, the valve means being electrically connected to the controller and being selectively actuatable to bypass the ultrafilter in response to the threshold signal.

14. An artificial kidney circuit according to claim 12 wherein the inlet chamber of the ultrafilter includes an outlet opening oriented to permit a portion of liquid therein to flow along the ultrafiltration membrane and exit the inlet chamber without passing through the ultrafiltration membrane.

15. An artificial kidney circuit according to claim 14 wherein the outlet opening of the inlet chamber is flow connected to the outlet line.

16. An artificial kidney circuit according to claim 12 further including a flow meter located in the connecting line and being electrically connected to the controller.

17. An artificial kidney circuit according to claim 12 further including a circulation pump located in the connecting line and electrically connected to the controller.

18. An artificial kidney circuit according to claim 12 further including a circulating pump located in the inlet line and being electrically connected to the controller.

19. An artificial kidney circuit, the circuit comprising:
    a haemodialyzer having a dialysate compartment and a blood compartment separated from the dialysate compartment by a dialysis membrane;
    an ultrafilter having an inlet chamber, an outlet chamber, and an ultrafiltration membrane separating the inlet chamber from the outlet chamber;
    an inlet line for flow connecting the inlet chamber to a source of dialysis liquid;
    an outlet line for flow connecting the outlet chamber to the dialysate compartment of the haemodialyzer;
    a branch line for bypassing the ultrafilter, the branch line having a first end flow connected through a first valve to the inlet line and second end flow connected through a second valve to the outlet line; and
    means for checking the membrane of the ultrafilter, the checking means including means for determining pressure on opposite sides of the membrane, and for calculating a transmembrane pressure therefrom, means for storing a predetermined transmembrane pressure threshold value, and control means for comparing the calculated transmembrane pressure with the predetermined threshold value and for generating a threshold signal when the calculated transmembrane pressure reaches the predetermined threshold value.

20. An artificial kidney circuit responsive to a transmembrane pressure threshold value the circuit comprising:
    an ultrafilter having an inlet chamber, an outlet chamber, and an ultrafiltration membrane separating the inlet chamber from the outlet chamber;
    a haemodialyzer having a dialysate compartment and a blood compartment separated from the dialysate compartment by a dialysis membrane;
    an inlet line for flow connecting the inlet chamber to a source of dialysis liquid;
    an outlet line for flow connecting the outlet chamber to the dialysate compartment of the haemodialyzer;
    a branch line for bypassing the ultrafilter, the branch line having a first end flow connected to the inlet line and second end flow connected to the outlet line;
    valve means for selectively diverting fluid flow from the inlet line into the branch line; and
    means for continuously checking the membrane of the ultrafilter while dialysis liquid flows from the source through the ultrafilter and the haemodialyzer to determine the existence of breaks and clogs, the checking means including means for determining pressure on opposite sides of the membrane, and for calculating a transmembrane pressure therefrom, means for storing the transmembrane pressure threshold value, and control means for comparing the calculated transmembrane pressure with the stored threshold value and for generating a threshold signal when the calculated transmembrane pressure reaches the threshold value.

* * * * *